United States Patent
Kirsch et al.

[11] Patent Number: 6,116,904
[45] Date of Patent: Sep. 12, 2000

[54] ENDOSTEAL SINGLE TOOTH IMPLANT SECURED AGAINST TORSION, STAMPING TOOL AND POSITIONING AID FOR PRODUCING SUCH A SINGLE TOOTH IMPLANT

[75] Inventors: Axel Kirsch, Filderstadt; Walter Dürr, Remchingen, both of Germany

[73] Assignee: IMZ Fertigungs- und Vertriebsgesellschaft für dentale Technologie mbH, Filderstadt, Germany

[21] Appl. No.: 09/242,577
[22] PCT Filed: May 5, 1997
[86] PCT No.: PCT/DE97/00460
    § 371 Date: Feb. 18, 1999
    § 102(e) Date: Feb. 18, 1999
[87] PCT Pub. No.: WO98/07382
    PCT Pub. Date: Feb. 26, 1998

[30] Foreign Application Priority Data

Aug. 21, 1996 [DE] Germany ............ 196 33 570

[51] Int. Cl.[7] ............... A61C 8/00; B21D 28/00
[52] U.S. Cl. ................................................. 433/173
[58] Field of Search ............................. 433/172, 173, 433/174

[56] References Cited

U.S. PATENT DOCUMENTS

| | | | |
|---|---|---|---|
| 5,125,840 | 6/1992 | Dürr et al. ............... | 433/173 |
| 5,195,892 | 3/1993 | Gersberg ................ | 433/174 |
| 5,316,477 | 5/1994 | Calderon ............... | 433/173 |
| 5,577,912 | 11/1996 | Prins .................... | 433/172 |

FOREIGN PATENT DOCUMENTS

40 28 855 3/1992 Germany.
41 27 839 3/1992 Germany.

*Primary Examiner*—Ralph A. Lewis
*Attorney, Agent, or Firm*—Hill & Simpson

[57] ABSTRACT

Endosteal individual tooth implant for a snug tooth replacement, having an essentially cylindrical basic element that can be placed in a bore made in a jaw bone, which basic element has a blind bore open at its coronal end, and with a spacer sleeve that can be placed on the coronal frontal edge of the basic element so as to be secured against rotation, which sleeve has a cervical centering collar that can be placed into a hollow cylindrical annular opening provided at the coronal end of the basic element, and a shoulder that is attached to the centering collar in the coronal direction and that can be placed onto the coronal frontal edge of the basic element. The sleeve has a bore, open at its coronal end, for receiving an implant post that can be placed directly or indirectly into the blind bore of the basic element and that penetrates at least partially the spacer sleeve, and is provided with a fastening head for the tooth replacement, replacement. A first number of coronally open basic element positive-lock grooves are arranged in the inner wall of the hollow cylindrical annular opening, immediately following the frontal edge of the basic element, and the grooves preferably having a regular spacing in relation to the circumference of the basic element, and a second number of spacer sleeve positive-lock cams, fashioned complementary to the basic element positive-lock grooves, are arranged, preferably with a regular spacing in relation to the circumference of the spacer sleeve, on the outer wall of the centering collar in a positive-lock segment whose outer diameter corresponds to the inner diameter of the basic element in the area of the basic element positive-lock grooves. The second number before the due placement of the spacer sleeve into the basic element is a whole-number multiple of the first number, and the spacer sleeve positive-lock cams or keys are selectively removed by a stamping tool to match the grooves of the basic element.

13 Claims, 5 Drawing Sheets

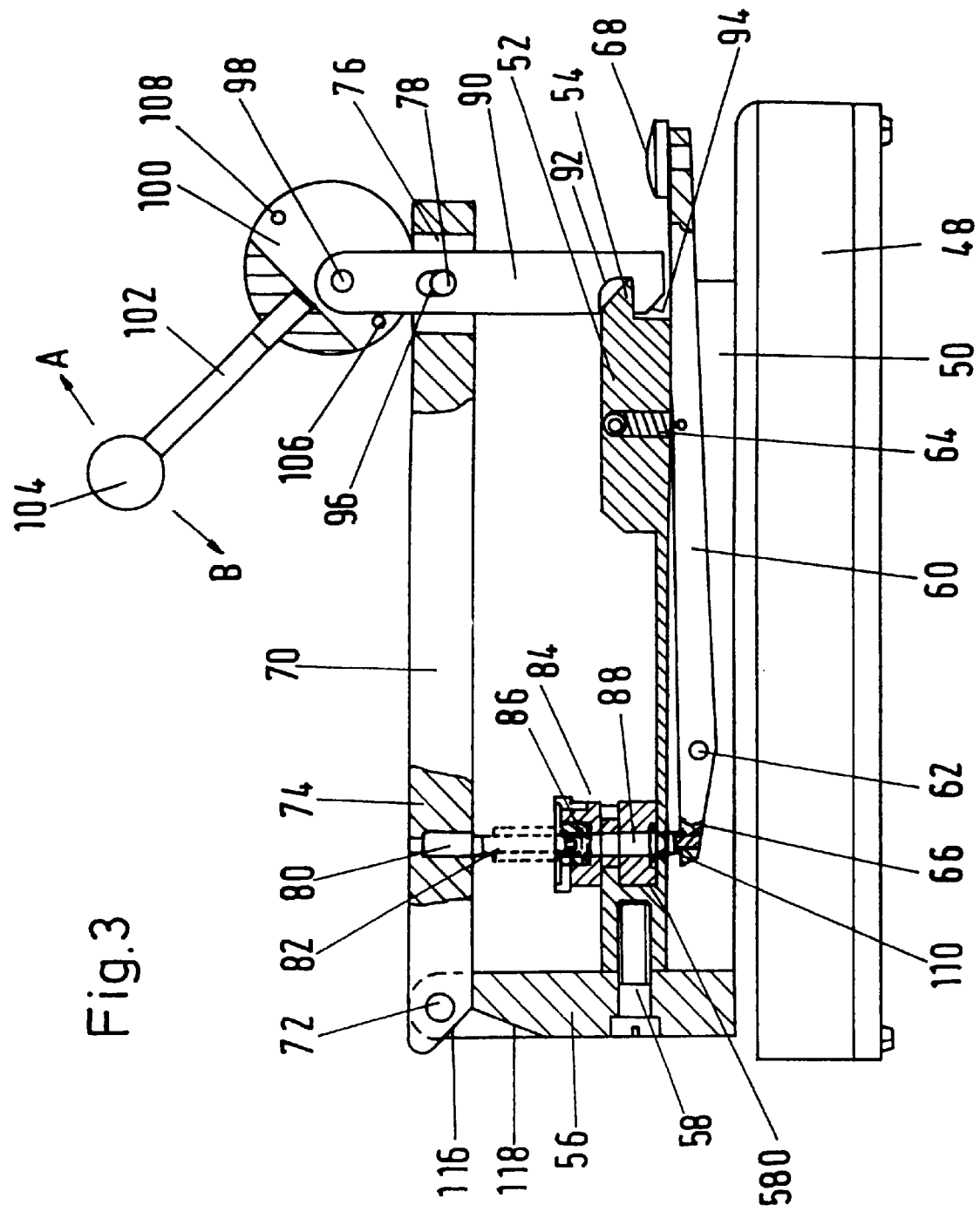

ENDOSTEAL SINGLE TOOTH IMPLANT SECURED AGAINST TORSION, STAMPING TOOL AND POSITIONING AID FOR PRODUCING SUCH A SINGLE TOOTH IMPLANT

BACKGROUND OF THE INVENTION

The invention relates to an endosteal individual tooth implant for a snug tooth replacement, which implant has an essentially cylindrical basic element that can be placed in a bore made in a jaw bone and, which basic element has a blind bore open at its coronal or upper end. The implant includes a spacer sleeve that can be placed on the coronal frontal edge of the basic element so as to be secured against rotation, which sleeve comprises a cervical centering collar that can be placed into a hollow cylindrical annular opening provided at the coronal end of the basic element, and comprises a shoulder that can be placed onto the coronal frontal edge of the basic element. The sleeve has a bore, open at its coronal end, for receiving an implant post that can be placed directly or indirectly into the blind bore of the basic element and that penetrates at least partially the spacer sleeve, and that forms a fastening head for the tooth replacement. The implant has a first number of coronally open basic element positive-lock grooves provided in the inner wall of the hollow cylindrical annular opening, immediately following the frontal edge of the basic element, which grooves are preferably arranged in a regular division or spacing in relation to the circumference of the basic element, and the implant has a second number of spacer sleeve positive-lock cams, fashioned so as to be complementary to the basic element positive-lock grooves, which cams are arranged (with a preferably regular division in relation to the circumference of the spacer sleeve) on the outer wall of the centering collar in a positive-lock segment whose outer diameter corresponds to the inner diameter of the basic element in the area of the basic element positive-lock grooves.

In addition, the invention relates to a stamping tool, as well as a positioning aid for manufacturing such an individual tooth implant, in particular its spacer sleeve.

An individual tooth implant of the type described above is the subject matter of the German patent application 195 34 979.2 which has positive-lock grooves in the basic element of the implant, whose number predetermines the fine division and work together with an equal or smaller number of projections or, respectively, cams on the spacer sleeve to prevent rotation between the sleeve and basic element. Given components on the implant that are not rotationally symmetrical, as predetermined for example by the spacer sleeve, it is required in principle to graduate the angular positions as tightly as possible. Given the use of an above-described implant, it is possible to offset the spacer sleeve to the basic element in angular steps of 30°, and thereby to align it as desired. However, this fine division also involves the risk of a rotated installation, connected with a possible wrong alignment and positioning, whose evaluation is difficult in the oral cavity in some circumstances. This holds in particular given several implants to be installed simultaneously in the patient's mouth. A wrong positioning leads to biomechanical and physiological stress on the implant, resulting in bone loss around the implant. Loss of the implant is possible as a final consequence in this situation. In addition, the possibility of fine alignment forms an optimal aesthetic care from the prosthetic point of view.

SUMMARY OF THE INVENTION

The underlying object of the invention is to construct the individual tooth implant described above in such a way that, without limitation of the fine alignment properties, the positioning possibilities during use in the patient's mouth is reduced in comparison with the number of fine alignment possibilities, so that the danger of a wrong alignment in the patient's mouth is practically excluded.

This object is achieved in that the second number before thee insertion of the spacer sleeve in the patient's mouth is a whole-number multiple of the first number; and that prior to inserting the spacer sleeve into the basic element the spacer sleeve positive-lock cams are reduced at least one and at the most to a number corresponding to the first number of basic element positive-lock grooves, whereby only those spacer sleeve positive-lock cams finally remain on the spacer sleeve that, during insertion of the spacer sleeve, engage in basic element positive-lock grooves in the desired alignment to the basic element.

In a preferred embodiment, the basic element positive-lock grooves extend parallel to the longitudinal axis of the basic element, and have a cross-section that is essentially a circular segment in a radial plane.

It is thereby particularly preferred that at least one of the basic element positive-lock grooves comprises a guide surface at the coronal end or outer.

In addition, it can be provided that at least one of the spacer sleeve positive-lock cams is fashioned so as to taper in the cervical direction from the cam root, whereby at least one positive-lock cam diameter near the cam root, measured in a radial plane, is slightly larger than a corresponding diameter of at least one allocated basic element positive-lock groove near the frontal edge of the basic element.

In principle, the inventive solution of the task is possible with only one basic element positive-lock groove and only one spacer sleeve positive-lock cam. However, in practice it has turned out that the number of basic element positive-lock grooves should preferably be three, and that of the spacer sleeve positive-lock cams should preferably be twelve. This reduced number of the basic element positive-lock grooves—from twelve, corresponding to the implant specified in the patent application 195 09 762.9-32, to here e.g. three—offers considerable mechanical advantages, because the wall thickness of the basic element can be maintained over a large surface. This leads to increased strength between the implant and the spacer sleeve. For the finished individual tooth implant, after the determination of the exact alignment of the twelve spacer sleeve positive-lock cams, nine are removed. In this way there results a spacer sleeve which, in combination with the basic element with three basic element positive-lock grooves, allows only angular steps of 120°.

With the inventive individual tooth implant, the possibility of fine division in the preparation phase is thus maintained, while during the placement in the patient's mouth the correct alignment is easy to determine. At the same time, a high degree of physical rotational stability is achieved in the preferred embodiment.

In the individual tooth implant according to the invention, it is always important that the centering collar fit as precisely as possible into the threading of the annular opening of the basic element, as specified in the German patent application 195 09 762.9-32 (which does not enjoy prior publication), whereby an optimal strength is ensured due to the positive and frictional locking of the spacer sleeve and thereby also of the tooth replacement in relation to the basic element.

In addition, in the embodiment of the invention in which the positive-lock cams of the spacer sleeve are fashioned so as to taper cervically, the stability and precision of the connection between the basic element and the spacer sleeve are further enhanced in that by this means manufacturing-related tolerances in the interplay between the positive-lock grooves and the positive-lock cams are compensated, and an unproblematic snug fit of the positive-lock cams in relation to the positive-lock grooves is ensured.

In order to remove the superfluous spacer sleeve positive-lock cams, it is useful to use a special stamping tool distinguished by a receptacle means for the spacer sleeve and a cutting means, whereby the cutting means comprises an essentially annular blade whose diameter corresponds to the diameter of the positive-lock segment of the spacer sleeve, and in which openings are arranged whose number corresponds to that of the basic element positive-lock grooves, and whose distance, measured along the pitch circle, corresponds at least to the distance measured along the pitch circle of a spacer sleeve positive-lock cam at its support surface on the spacer sleeve.

The use of a positioning aid that avoids the danger of the stamping of false cams is likewise useful. A positioning aid is suitable for this purpose that has a bearer comprising an opening through which the spacer sleeve placed therein extends, and is held, whereby positioning grooves are provided in the opening that correspond in their arrangement to the basic element positive-lock grooves of the basic element that is used with the spacer sleeve.

Particularly preferably, markings are provided on the bearer that indicate the division of the spacer sleeve positive-lock cams, and that are used in particular together with "dummy" superstructures for the precise determination of position.

Further features and advantages of the invention result from the following specification, in which embodiments are explained in detail on the basis of the schematic drawings.

BRIEF DESCRIPTION OF THE DRAWINGS

FIG. 3 is a side view with portions broken away of a stamping tool;

DESCRIPTION OF THE PREFERRED EMBODIMENTS

Figure 1:
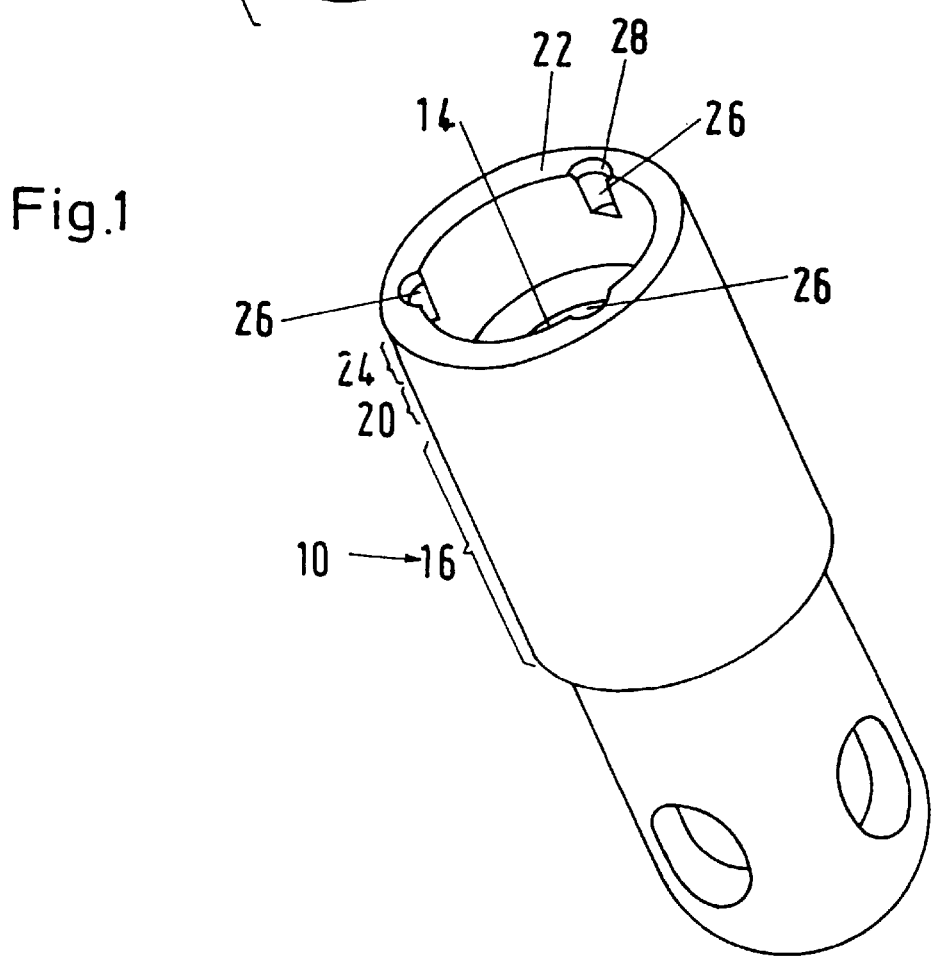
FIG. 1 is a perspective view of an embodiment of the basic element of the endosteal individual tooth implant according to the invention.

As can be seen from FIG. 1, in the embodiment shown there the individual tooth implant comprises a basic element 10 of a known type, as specified for example in DE-PS 40 28 855 and also in the already-mentioned German patent application 195 34 979.2. The basic element 10, fashioned so as to be closed at its cervical or lower end (shown at the bottom in FIG. 1), comprises a blind bore open towards its coronal end or upper, located at the top in FIG. 1. Near the cervical end of the blind bore, there is an inner threading (not visible in the Figure) with a relatively small diameter, into which an implant post (not graphically shown in FIG. 1) can be screwed. There follows an annular opening 14 with a diameter that is enlarged in relation to the inner threading. The annular opening 14 comprises a centering region 16 connected coronally to the inner threading. A guide region 20 is connected to this centering region in the coronal direction, in which guide region the annular opening 14 has a smooth hollow cylindrical inner wall, with a diameter that is again enlarged. A positive locking region 24 of the annular opening 14 extends from the guide region 20 up to a coronal frontal edge 22 of the basic element 10, in which a number of axial positive-lock grooves 26 (three in the embodiment shown in FIG. 1) are incorporated into the inner wall of the annular opening 14. The positive-lock grooves 26 extend parallel to the longitudinal axis of the basic element 10, and have in a radial plane a cross-section that is essentially in the shape of a circular segment. Each of the positive-lock grooves 26 comprises at its coronal end, i.e. the end facing the frontal edge 22, a guide surface 28 that leads, as a conical bevel going out from the frontal edge 22, into the part of the positive-lock grooves 26 that subsequently runs in the axial direction with straight walls.

Figure 2:
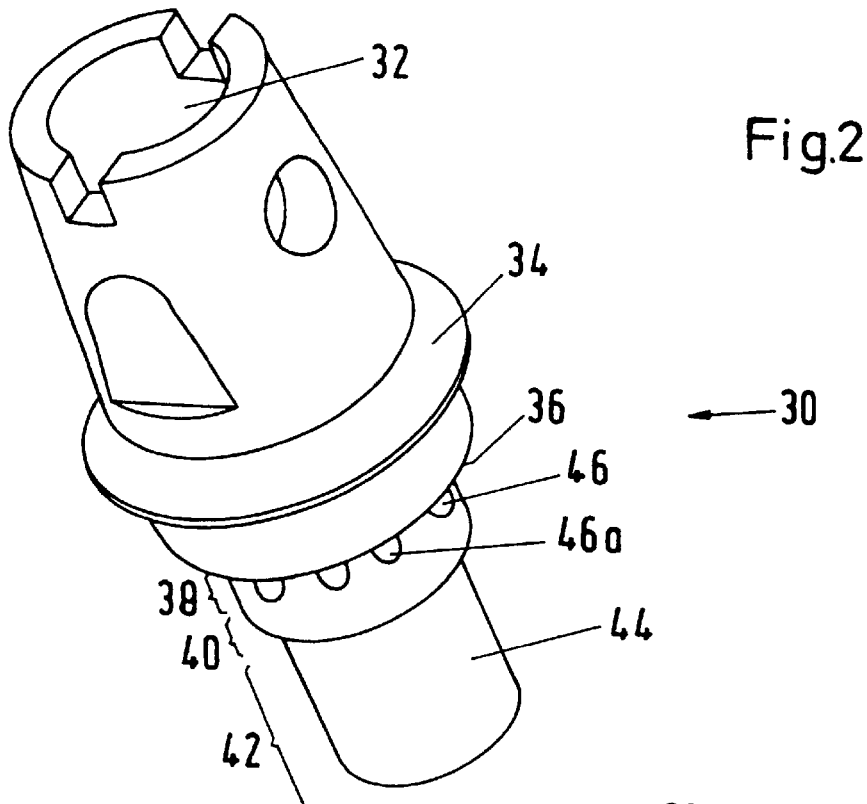
FIG. 2 is a perspective view of a spacer sleeve corresponding to FIG. 1.

A spacer sleeve 30, shown in FIG. 2, serves in the manner shown in the German patent application 195 09 762.9 as a fastening head for a snug tooth replacement (not shown). The spacer sleeve 30 is provided with an axial longitudinal bore 32 whose inner diameter corresponds to the outer diameter of the implant post (not shown). In addition, it is provided with a circumferential support shoulder 34 for the tooth replacement. Following a shoulder 36 that can be placed on the frontal edge 22 of the basic element 10, which shoulder is fashioned as a circumferential annular shoulder, the spacer sleeve 30 comprises, in the cervical direction, a positive-lock segment 38, a guide segment 40 and a centering segment 42 of a centering collar 44. In the positive-lock region 38, a number of positive-lock cams keys or projections 46, 46a that extend in the axial and radial direction are provided, whereby this number is a whole-number multiple of the number of basic element positive-lock grooves 26. In the representation according to FIG. 2, of the spacer sleeve positive-lock cams 46, 46a provided for this embodiment only four can be seen, whereas their number on the circumference of the positive-lock region 38 can actually be twelve. Each of the spacer sleeve positive-lock cams 46 corresponds in its shape (except for the guide surfaces 28) to the positive-lock grooves 26 of the basic element 10.

During placement of the spacer sleeve 30 into the basic element 10, the centering segment 42 of the centering collar 44 engages in the centering region 16 of the annular opening 14. The guide segment 40 of the spacer sleeve 30 sits with a snug fit in the guide region 20 of the basic element 10.

Of the spacer sleeve positive-lock cams 46, the ones are removed—in the manner to be described in more detail below—whose position would not correspond to the basic element positive-lock grooves 26, given a correct alignment of the spacer sleeve 30 on the basic element 10. During the further placement of the spacer sleeve 30, the remaining positive-lock cams, e.g. the positive-lock cam 46, then engage in the basic element positive-lock grooves 26, while the shoulder 36 comes to rest on the frontal edge 22. In this way the spacer sleeve 30 is connected in rotationally secured fashion with the basic element 10. By means of the implant post, which is screwed into the inner threading of the basic element 10, the spacer sleeve 30 can be connected in a fixed manner with the basic element 10.

A stamping tool for the removal of the unnecessary spacer sleeve guide cams is shown in FIG. 3 in a partially sectional side view. A base 50 is determined on a substructure 48 provided with feet, said base having a cross-section that is essentially T-shaped, whereby the segments running parallel to the substructure 48 are constructed with different thickness according to requirements with respect to function and stability, as is explained in more detail below. At a first end segment of the T-base 50, a stay 56 is arranged that protrudes vertically from the substructure 48 and is fixedly connected by means of a screw 58 with the segment of the base 50, which is fashioned in correspondingly massive fashion. The receptacle means for a spacer sleeve is also located in this region, which means consists essentially of a positioning cap 84 with a matrix, specified in more detail in FIG. 5, in which if necessary a positioning aid, to be specified later, is placed, and which is placed into the base 50 in a notch 580 and is held therein. A longitudinal bore 86 runs through the positioning cap 84, which bore continues into the base 50 and into which a pin 88 is placed that works together with an ejector lever 60 in a way to be described later. The longitudinal bore 86 thereby debouches in an arm of the base 50 that runs parallel to the substructure 48. Connected to a transition piece in which the segments of the base 50 are fashioned relatively thin, a massive projection 52, ending in a tab 54, is provided on the end of the base 50 opposite the screw 58. In a blind opening of the projection 52 open at the substructure 48, a retaining spring 64 is secured whose free end engages with the already-mentioned ejector lever 60. The ejector lever 60 can be pivoted about an axle of rotation 62 that is arranged near the receptacle means for the spacer sleeve. At the free end of this relatively short lever arm of the ejector lever 60 there is located an opening 66 in which a plunger 110 is placed that is aligned with the longitudinal bore 86 of the positioning cap 84 and that acts on the pin 88. By means of the retaining spring 64, which engages with the longer lever of the ejector lever 60, the ejector lever 60 is held in such a way that the plunger 110 exerts no force on the pin 88. When an operator presses on the button 68 on the free end of the longer lever arm of the ejector lever 60, this lever rotates about its axle 62 in such a way that the plunger 110 in drawn into the longitudinal bore 86, and a spacer sleeve placed approximately in the positioning cap 84 slides out therefrom. This process is specified more precisely with reference to FIG. 5.

At the outer end (at the top in FIG. 3) of the stay 56, a pressure lever 70 is coupled in such a way that it can be pivoted about an axle of rotation 72 located in the vicinity of its one end. In the operating state, lying over the positioning cap 84, a pressure implant 80 that carries a plunger 82 is placed into a bored hole 74. The free end of the pressure lever 70 opposite the axle of rotation 72 comprises an opening 76 that runs from top to bottom in the drawing, through which an arm 90 hangs from an axial rod 78 that is arranged in the opening 76 and that is guided on the other hand with a longitudinal slot 96 arranged in the arm 90, whose longer dimension runs perpendicular to the axial rod 78. The end of the arm hanging in the direction towards the substructure 48 comprises an opening 92 that faces the base 50, in particular the tab 54 thereof, and receives this tab in the operating state of the stamping tool. Underneath the opening 92, the hanging end of the arm 90 additionally comprises a beveling 94 that, as shown in FIG. 3, runs parallel to the beveled surface of the tab 54. The free end of the arm 90, opposite the hanging end, forms an axle of rotation 98 to which a rotating disk 100 is coupled eccentrically. A lever rod 102 that bears an operating knob 104 is screwed into the rotating disk 100. Two pins 106, 108 attached to the rotating disk 100 form rotational limits for the motion of the rotating disk 100.

FIG. 3 shows the stamping tool in a state in which a previously used spacer sleeve has been stamped precisely in the desired manner. In order now to remove the spacer sleeve, the rotating disk 100 is further pivoted in the direction of the arrow B with the aid of the lever rod 102 or, respectively, of the operating knob 104, so that the previously fixed seating of the axial rod 78 at the end of the elongated slot 96 pointing to the substructure 48 is given up. The axial rod 78 now no longer operates exclusively as a guide, but rather also as an axle of rotation about which the arm 90 can be pivoted with play between the tab 54 and the recess 92, by means of the action of the pin 106, and the locking between the arm 90 and the base 50 is thereby released. The pressure lever 70 can now be pivoted about the axle of rotation 72 until its seating surface 116 on the end coupled to the axle of rotation 72 is applied to a corresponding seating surface 118 of the stay 56. With the aid of the ejector lever 60, the finished spacer sleeve can then be lifted and removed from the positioning shoulder in the manner described above, a new spacer sleeve can be put in place, and the stamping tool can be closed again by pivoting the pressure lever 70 back into its operating position. The arm 90 hanging from the pressure lever 70 then lies at first with its bevel 94 on the obliquely running surface of the tab 54, and in the further course of the motion snaps with the opening 92 via the tab 54. The tool is then ready for a further stamping process, for which the rotating disk 100 is to be rotated in the direction of the arrow A until the rotation is limited by the application of the axial rod 78 on the edge (pointing to the substructure 48) of the elongated slot 96 in the arm 90. The pin 108 forms a rotational limit for this motion.

Figure 4:
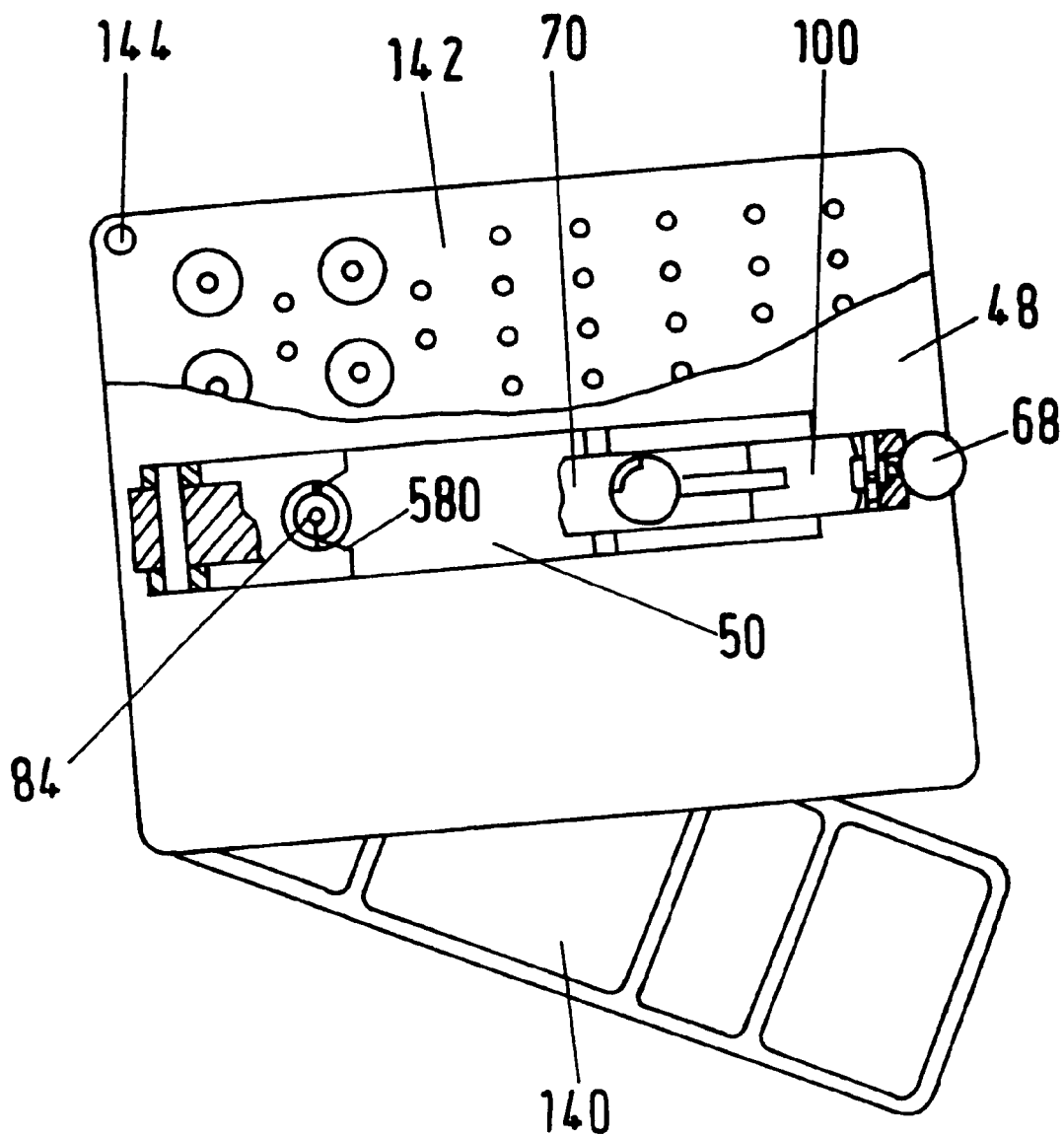
FIG. 4 is a top view with portions broken away of the stamping tool of FIG. 3.

FIG. 4 shows in particular, in a top view of the stamping tool of FIG. 3, details of the substructure 48 formed as a hollow element, shown partially open. The base 50 is fastened to the substructure 48 by means of screws or the like (not shown). On both sides of this fastening means, magazines 140, 142 are provided for small parts, replacement matrices, etc., which, as shown for the magazine 142, can be pivoted out from the substructure 48 about a pivot bolt 144. A pivot stop in the form of a pin (not shown) can be provided on the floor of the respective magazine 140, 142.

The notch 580, which interchangeably receives the positioning cap 84, can be seen particularly clearly in FIG. 4.

Figure 5:
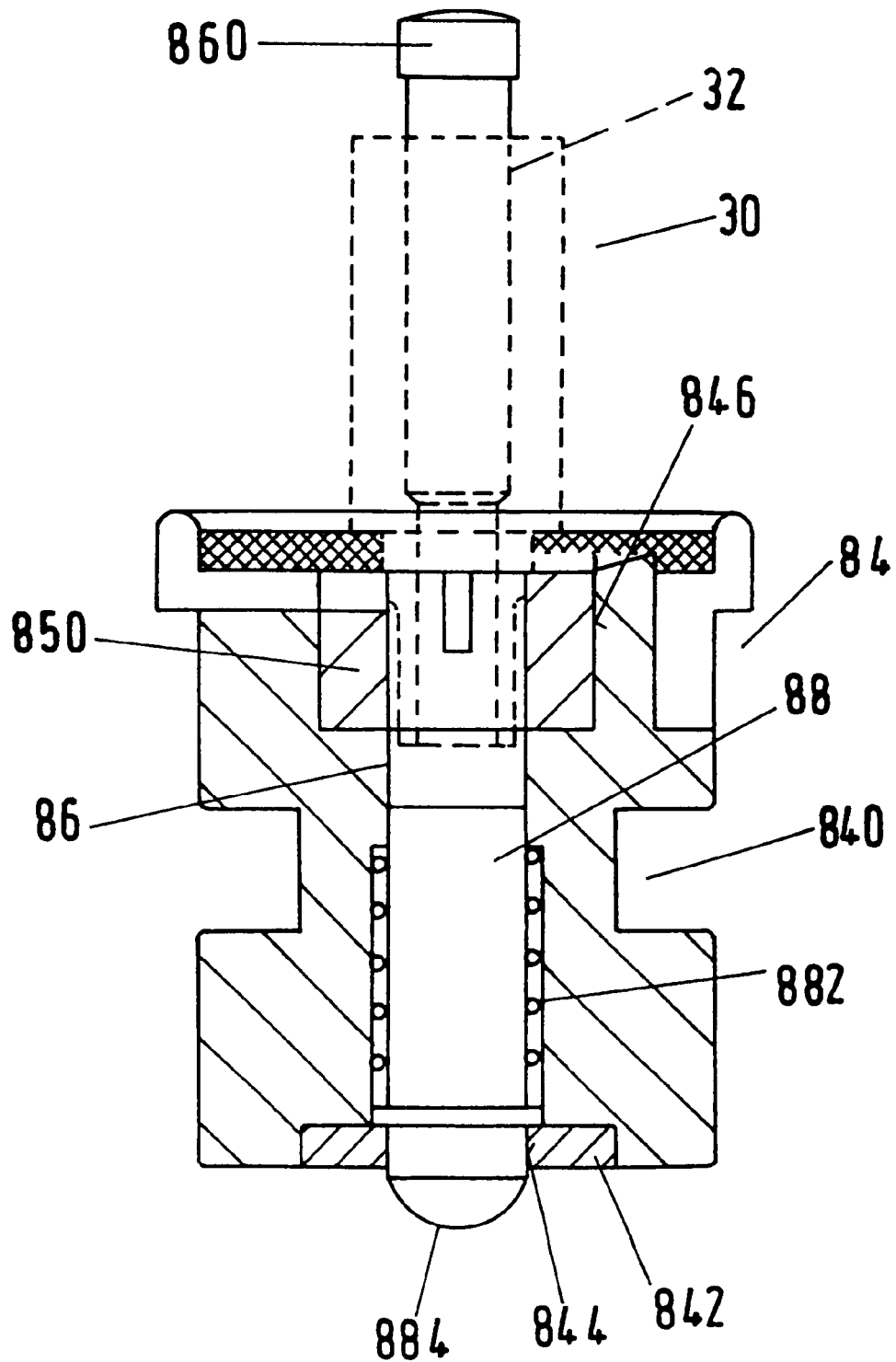
FIG. 5 is an axial longitudinal cross sectional view of a receptacle means and of a cutting means for a stamping tool.

The positioning cap 84, shown in axial longitudinal section in FIG. 5, is essentially hollow and cylindrical, and comprises a constriction 840 approximately in the center of its axial length. In the longitudinal bore 86 through the shoulder, there is a pin 88 that is loaded by a spiral spring 882 supported in the interior of the longitudinal bore 86, which pin is held in the longitudinal bore 86 by a pressure plate 842 provided in a recess in the positioning cap 84 at its end later facing the ejector lever (60 in FIG. 3) and which protrudes through an opening 844 provided in the pressure plate 842. This protruding segment 884 of the pin is fashioned so as to be crowned. During the placement of the positioning cap 84 into the notch 580, the crowned segment 884 snaps into the opening of the base 50 that is specified in connection with FIG. 3, which opening continues the longitudinal bore 86. The positioning cap 84 cannot be removed until the plunger 110 of the ejector lever 60 (FIG. 3) pushes the pin 88 back into the interior of the longitudinal bore 86, after a spacer sleeve 30 located approximately in the positioning cap 84 has been lifted out.

The cutting means 850 is arranged in a recess or receptacle 846 in the positioning cap and faces the pressure lever 70 while in the assembled state so that the cutting means 850 will cut off the unnecessary positive-lock cams of an installed spacer sleeve 30. The cutting process is thereby supported by a pressure pin 860 that is guided through the longitudinal bore 32 of the spacer sleeve 30 and on which the plunger 82 of the pressure implant 80 acts.

Figure 6:
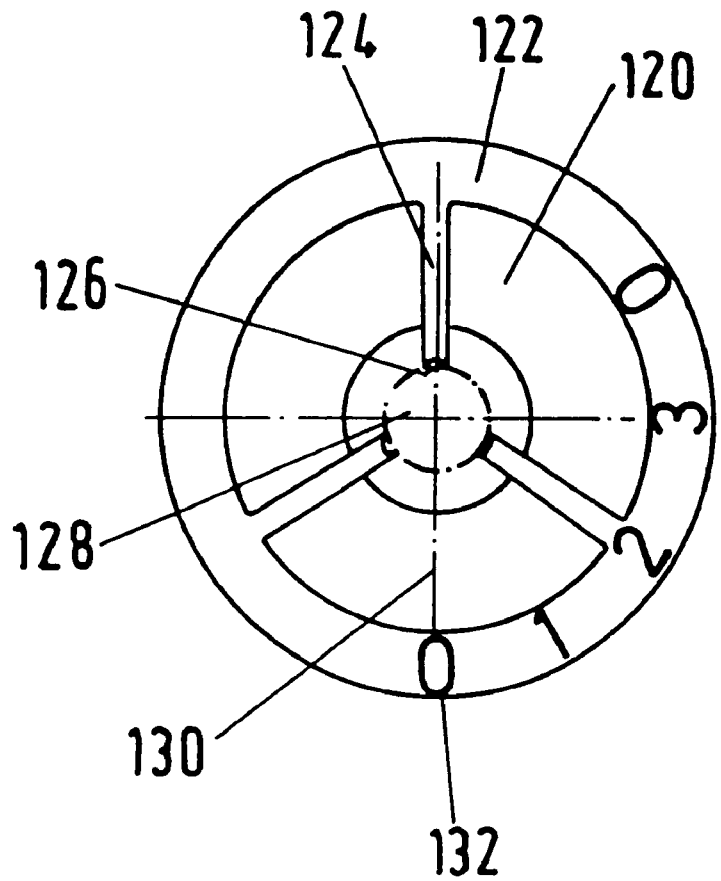
FIG. 6 is a top view of a positioning aid.
Figure 7:
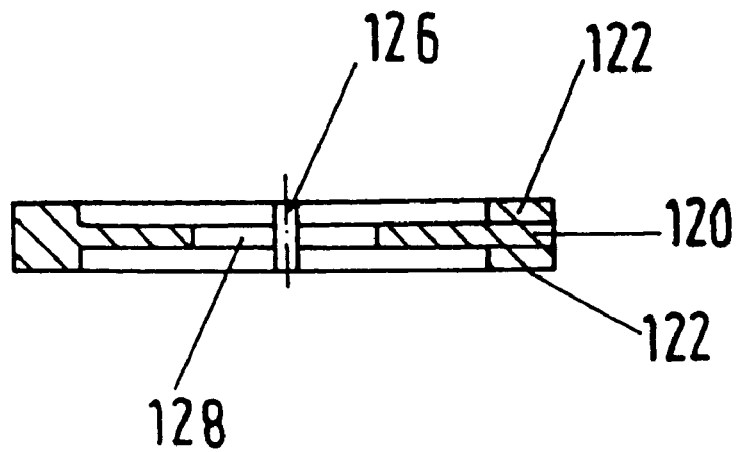
FIG. 7 is the positioning aid of FIG. 6 in an axial longitudinal sectional view.

FIGS. 6 and 7 show, in a top view or, respectively, in longitudinal section, a positioning aid for use in the invention, as is then used for example in the positioning cap 84 of the stamping tool shown in FIGS. 3 and 4. The positioning aid consists of a circular bearer 120 that is provided with annular reinforcements 122 on its upper and lower side at the outer edge. According to the construction of the basic element for which the spacer sleeve is to be manufactured, arms 124 extending out from the reinforcements 122 are fashioned at positions corresponding to the basic element positive-lock grooves, the free ends of said arms being located over an opening 128 and ending in positioning grooves 126 whose shape corresponds to the basic element positive-lock grooves. The spacer sleeve positive-lock grooves that are to be taken out by the stamping process thereby lie unprotected in the positioning aid. The markings 130 or, respectively, 132 made on the reinforcement 122 serve for the determination of angular positions. Locating marks 130 are thereby plotted at an angular spacing of 30°. The numerical indications, reference number 132, then represent the actual positioning aids. These are used in connection with what are called dummy structures. Given a division of 30° in the spacer sleeve positive-lock cams, five such dummy structures are required in order to determine the possible angular positions—one for the position 0° (marking 2 as positioning aid), one for the position −30° (marking 1), a further one for the positioning −60° (marking 0, read further in the clockwise direction on the reinforcement 122), a fourth one for the positioning +30° (marking 3) and a fifth one for the positioning +60°, which corresponds in turn to the marking 0.

If the precise alignment has been determined with the aid of the dummies, the spacer sleeve can be put in place according to the corresponding marking in the positioning aid, so that the cams, which are required later in the implant, lie protected in the grooves 126.

The features of the invention disclosed in the above specification, in the drawing and in the claims can be essential for the realization of the invention both individually and also in arbitrary combination.

We claim:

1. Endosteal individual tooth implant for a snug tooth replacement, having an essentially cylindrical basic element that can be placed in a bore made in a jaw bone, which basic element has a blind bore open at its coronal end, and a spacer sleeve that can be placed on a coronal frontal edge of the basic element so as to be secured against rotation, which sleeve comprises a cervical centering collar that can be placed into a hollow cylindrical annular opening of the blind bore of the basic element, said sleeve having a shoulder that is attached to the centering collar in the coronal direction and that can be placed onto the coronal frontal edge of the basic element, said sleeve having a bore, open at its coronal end, for receiving an implant post that can be placed directly or indirectly into the blind bore of the basic element and that penetrates at least partially the spacer sleeve, and that is provided with a fastening head for the tooth replacement, a first number of coronally open basic element positive-lock grooves being arranged in the inner wall of the hollow cylindrical annular opening, immediately following the frontal edge of the basic element, said grooves preferably having a regular spacing in relation to the circumference of the basic element, and a second number of spacer sleeve positive-lock cams being fashioned complementary to the basic element positive-lock grooves and being arranged with a regular spacing in relation to the circumference of the spacer sleeve on the outer wall of the centering collar in a positive-lock segment whose outer diameter corresponds to the inner diameter of the basic element in the area of the basic element positive-lock grooves, the second number before the due placement of the spacer sleeve into the basic element being a whole-number multiple of the first number, and the spacer sleeve positive-lock cams at least being removed to leave one and at most a number that corresponds to the first number of basic element positive-lock grooves so that only those spacer sleeve positive-lock cams finally remaining on the spacer sleeve engage in the basic element positive-lock grooves in the desired alignment to the basic element during insertion of the spacer sleeve into the basic element.

2. Individual tooth implant according to claim 1, wherein the number of spacer sleeve positive-lock cams finally remaining on the spacer sleeve corresponds to the number of basic element positive-lock grooves.

3. Individual tooth implant according to claim 2, wherein the basic element positive-lock grooves extend parallel to the longitudinal axis of the basic element and have a cross-section in a radial plane that is essentially in the shape of a segment of a circle.

4. Individual tooth implant according to one of claim 1, wherein at least one of the basic element positive-lock grooves comprises a guide surface at the coronal end.

5. Individual tooth implant according to claim 3, wherein at least one of the spacer sleeve positive-lock cams is fashioned so as to taper in the cervical direction from the cam root, whereby at least one positive-lock cam diameter near the cam root, measured in a radial plane, is slightly larger than a corresponding diameter of at least one allocated basic element positive-lock groove near the frontal edge of the basic element.

6. Individual tooth implant according to claim 1, wherein the first number is three.

7. Individual tooth implant according to claim 6, wherein the second number is twelve.

8. An endosteal individual tooth implant according to claim 1, wherein the second number is twelve.

9. An endosteal individual tooth implant according to claim 1, wherein the basic element positive-lock grooves extend parallel to the longitudinal axis of the basic element and have a cross section in a radial plane that is essentially in the shape of a segment of a circle.

10. An endosteal individual tooth implant according to claim 9, wherein at least one of the basic element positive-lock grooves has a guide surface at the coronal end.

11. A stamping tool for manufacturing a spacer sleeve for an individual tooth implant, said spacer sleeve having a positive-lock segment with a cylindrical surface having positive-lock cams projecting therefrom with an even spacing, said tool comprising a receptacle means for receiving the spacer sleeve and cutting means for removing selected positive-lock cams, said cutting means including essentially annular blades having a diameter corresponding to the diameter of the positive-lock segment, said blades being arranged in an opening of the receptacle means with spacings therebetween with the number of spacings corresponding to the number of positive-lock grooves of a basic element and having a distance measured along a pitch circle corresponding at least to the distance measured along a pitch circle of a spacer sleeve positive-lock cam so that a selected number of positive-lock cams can be retained during the stamping operation.

12. A positioning aid for the manufacture of spacer sleeves of an individual tooth implant, said spacer sleeves having a positive-lock segment of a fixed diameter with a plurality of annularly spaced positive-lock cams extending therefrom, said positioning aid including a bearer having an opening through which the spacer sleeve placed therein protrudes and which holds the sleeve, wherein the positioning grooves are provided in the opening that correspond in this arrangement to basic element positive-lock grooves of the basic element that is being used with the spacer sleeve.

13. Positioning aid according to claim 12, wherein markings are made on the bearer that indicate the division of the spacer sleeve positive-lock cams.

* * * * *